United States Patent [19]
Archibald et al.

[11] 3,931,244
[45] Jan. 6, 1976

[54] THIOUREAS

[75] Inventors: John Leheup Archibald, Windsor; John Lambert Jackson, Henley-on-Thames, both of England

[73] Assignee: John Wyeth & Brother Limited, Maidenhead, England

[22] Filed: May 13, 1974

[21] Appl. No.: 469,145

[30] Foreign Application Priority Data
May 31, 1973 United Kingdom............... 26080/73

[52] U.S. Cl........... 260/347.2; 260/552 R; 424/322; 424/285
[51] Int. Cl.²...................................... C07D 307/68
[58] Field of Search...................... 260/347.2, 552 R

[56] References Cited
FOREIGN PATENTS OR APPLICATIONS
91,478    8/1959    Czechoslovakia

OTHER PUBLICATIONS

Tamchyna, Chemical Abstracts, Vol. 55, (1961), 3620c.

*Primary Examiner*—Henry R. Jiles
*Assistant Examiner*—Bernard I. Dentz

[57]             ABSTRACT

The invention relates to thioureas of formula:

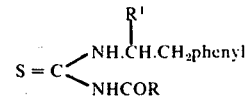

wherein R is phenyl, substituted phenyl or furyl and R¹ is hydrogen or methyl. The compounds are useful as anorexiants.

8 Claims, No Drawings

THIOUREAS

This invention relates to thioureas. More particularly the invention relates to certain N,N'-disubstituted-thioureas, to processes for preparing them and to pharmaceutical compositions containing them.

The present invention provides thioureas of the general formula (I)

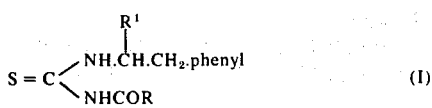

wherein R is phenyl, a phenyl radical substituted by one or more hydroxy, halo, lower alkyl, lower alkoxy or halo(lower)alkyl groups or a furyl radical (e.g. a 2-furyl radical) and $R^1$ is hydrogen or methyl.

The term "lower" as used herein means that the radical referred to contains up to 6, preferably up to 4, carbon atoms.

When the group R is a substituted phenyl group suitable substituents are hydroxy, halogen (for example, fluorine, chlorine or bromine, particularly chlorine), lower alkyl (for example methyl, ethyl, propyl or butyl, particularly methyl), lower alkoxy (for example methoxy, ethoxy, propoxy or butoxy, particularly methoxy) or halo(lower)alkyl (for example trifluoromethyl). Preferably R is a phenyl group containing a single substituent in the m or p position or, more preferably, an unsubstituted phenyl group. The group $R^1$ is preferably methyl.

A particularly preferred compound of general formula (I) is N-benzoyl-N'-(1-methyl-2-phenyl)ethylthiourea.

The thioureas of general formula (I) may be prepared by reacting an amine of general formula (II)

(wherein $R^1$ has the meaning given above) with an isothiocyanate of general formula (III)

R.CO.NCS      (III)

(wherein R has the meaning given above). The amine can be reacted with the isothiocyanate by methods known per se, for example the reactants may be heated together in a suitable solvent.

The isothiocyanates of general formula (III) are known compounds or they may be prepared by methods known for the preparation of analogous compounds. For example, they may be prepared by reacting a thiocyanate salt (e.g. ammonium thiocyanate or a metal thiocyanate such as an alkaline metal, alkaline earth metal or lead thiocyanate) with an acid halide of general formula (IV)

R.CO.X      (IV)

(wherein R has the meaning given above and X is a halogen atom, preferably chlorine). The isothiocyanate of general formula (III) need not be isolated from the reaction mixture but it can be reacted with the amine of general formula (II) in situ to yield the thiourea of general formula (I) directly.

When $R^1$ is methyl the compounds of the invention possess an asymmetric carbon atom and hence optical enantiomorphs are possible. The compounds of the invention may be in the form of the pure enantiomorphs or mixtures of such enantiomorphs such as racemates. The pure enantiomorphs may be obtained by reacting an optically active amine of general formula (II) with the isothiocyanate of general formula (III). If the amine is in the form of a mixture of enantiomorphs, such as a racemate, the product will likewise be a mixture of enantiomorphs.

The compounds of general formula (I) exhibit anorectic properties. Accordingly the invention further provides a pharmaceutical preparation comprising a compound of general formula (I) in association with a pharmaceutically acceptable carrier. According to another aspect the invention provides a method of inhibiting the appetite of a mammal by administering to the mammal an anorectic amount of a thiourea of general formula (I). Preferably the mammal is a human. The active compound may be administered in the form of a pharmaceutical composition.

The compounds of the invention may be tested for anorectic properties by the following procedure:

Groups of 8 or 10 male mice weighing 22–24 grams are starved overnight, although access to water is not restricted. The animals are dosed with the test drug or vehicle alone (control) one hour before they are placed individually into glass jars. The jars (100 mm diameter × 80 mm high) have lids fitted with a glass tube to accommodate a stick of spaghetti of approximate length of 450 mm. The glass tube is arranged such that only 5 mm of spaghetti is exposed for eating by the mouse. The length of spaghetti eaten during a two hour test period is indicative of the appetite of the animal.

When tested by this procedure at a dose of 100 mg/kg per os the following results were obtained:

| Compound of Example | % Inhibition* of appetite |
| --- | --- |
| 1 | 90 |
| 2 | 49 |
| 3 | 52 |
| 4 | 49 |
| 5 | 41 |
| 6 | 40 |
| 7 | 53 |

*determined by mean length eaten by control − mean length eaten by test animal / mean length eaten by control × 100

Generally the compounds, despite their advantageous anorectic properties, surprisingly have little or no undesirable stimulant activity, as measured by standard pharmacological tests.

Any suitable carrier known in the art can be used to prepare the pharmaceutical compositions of the present invention. The carrier may be solid, liquid or a mixture of solid and liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of compositions may be varied or adjusted from 5 mg. or less to 500 mg. or more, according to the particular need and the activity of the active ingredient. The invention also includes the compounds in the absence of carrier where the compounds are in unit dosage form.

The following examples illustrate the invention.

EXAMPLE 1

N-Benzoyl-N'-(1-methyl-2-phenyl)ethylthiourea.

Ammonium thiocyanate (4.00 g) was stirred in refluxing acetone (12 ml) and benzoyl chloride (7.0 g) added to the boiling solution over 5 min. Stirring was continued for 15 min. then d-amphetamine (6.76 g) in acetone (6 ml) was added dropwise, also with stirring. Reflux was maintained for a further 30 min., the mixture cooled and poured into cold water. The orange oil was extracted into ether (3 × 75 ml. portions), and the combined extracts washed with water, dried (MgSO$_4$), filtered and evaporated to give the title compound as a viscous orange/yellow oil (13.43 g), which crystallised on storing at 4°C for 24 hr. to give a solid, m.p. 68°–70°C.

Found: C, 68.31; H, 6.21; N, 9.72; C$_{17}$H$_{18}$N$_2$OS requires C, 68.42; H, 6.08; N, 9.39%,

EXAMPLE 2

N-Benzoyl-N'-phenthylthiourea.

Ammonium thiocyanate (4.00 g) and benzoyl chloride (7.00 g) were reacted together in the manner of Example 1. Phenethylamine (6.56 g) was then added and the mixture worked up, also as described in Example 1. The title compound was obtained as a yellow crystalline solid (14.41 g). Recrystallisation from ethanol/water afforded a colourless sample, m.p. 110.6°C.

Found: C, 67.57; H, 5.80; N, 9.70. C$_{16}$H$_{16}$N$_2$OS requires C, 67.57; H, 5.67; N, 9.58%

EXAMPLE 3

N-(4-Methoxybenzoyl)-N'-(1-methyl-2-phenyl)ethylthiourea.

Ammonium thiocyanate (2.00 g) and anisoyl chloride 4.27 g) were reacted together and the product treated with d-amphetamine (3.38 g) as described in Example 1. Work up afforded the crude title compound as a yellow sticky solid. Trituration with a little cold ether and filtration gave colourless needles, (0.93 g), m.p. 70.2°C.

Found: C, 65.82; H, 6.22; N, 8.49; C$_{18}$H$_{20}$N$_2$O$_2$S requires C, 65.84; H, 6.14; N, 8.53%

EXAMPLE 4

N-(3-Trifluoromethylbenzoyl)-N'-(1-methyl-2-phenyl)-ethylthiourea.

Ammonium thiocyanate (2.00 g) and m-trifluoromethylbenzoyl chloride (5.19 g) were reacted together and the product treated with d-amphetamine (3.38 g) in the manner of Example 1. Work-up afforded the title compound as a viscous oil (8.75 g).

Found: C, 58.36; H, 4.68; N, 7.46. C$_{18}$H$_{17}$F$_3$N$_2$OS. ¼H$_2$O requires C, 58.28; H, 4.76; N, 7.55%.

EXAMPLE 5

N-(4-Chlorobenzoyl)-N'-(1-methyl-2-phenyl)ethylthiourea.

Ammonium thiocyanate (2.00 g) and p-chlorobenzoyl chloride (4.38 g) were reacted together and the product treated with d-amphetamine (3.38 g) in the manner of Example 1. Work-up gave the title compound as a colourless crystalline solid (7.97 g) which was recrystallised as needles (7.34 g), m.p. 105.5°C, from ethanol.

Found: C, 61.60; H, 5.20; N, 8.69. C$_{17}$H$_{17}$ClN$_2$OS requires C, 61.34; H, 5.15; N, 8.42%.

EXAMPLE 6

N-Furoyl-N'-1-methyl-2-phenyl)ethylthiourea.

Ammonium thiocyanate (2.00 g) and furoyl chloride (3.23 g) were reacted together and the product treated with d-amphetamine (3.38 g) in the manner of Example 1. Work-up afforded the title compound as a pale yellow viscous oil (5.10 g).

Found: C, 62.14; H, 5.77; N, 9.47. C$_{15}$H$_{16}$N$_2$O$_2$S requires C, 62.49; H, 5.59; N, 9.72%.

EXAMPLE 7

N-(3-Toluoyl)-N'-(1-methyl-2-phenyl)ethylthiourea.

Ammonium thiocyanate (2.00 g) and m-toluoyl chloride (3.87 g) were reacted together and the product treated with d-amphetamine (3.38 g) in the manner of Example 1. Work-up afforded the title compound as a viscous, pale yellow oil (5.85 g).

Found: C, 69.16; H, 6.64; N, 8.86. $C_{18}H_{20}N_2OS$ requires C, 69.21; H, 6.45; N, 8.97%.

We claim:

1. A thiourea of the formula

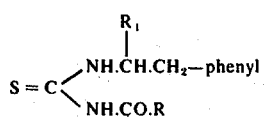

wherein R is selected from the group consisting of phenyl, furyl and phenyl monosubstituted by a member of the group consisting of halogen, lower alkyl, lower alkoxy and trifluoromethyl and $R^1$ is selected from the group consisting of hydrogen and methyl.

2. A thiourea as claimed in claim 1 which is N-benzoyl-N'-(1-methyl-2-phenyl)ethylthiourea.

3. A thiourea as claimed in claim 1 which is N-benzoyl-N'-phenethylthiourea.

4. A thiourea as claimed in claim 1 which is N-(4-methoxy-benzoyl)-N'-(1-methyl-2-phenyl)ethylthiourea.

5. A thiourea as claimed in claim 1 which is N-(3-trifluoro-methylbenzoyl)-N'-(1-methyl-2-phenyl)ethylthiourea.

6. A thiourea as claimed in claim 1 which is N-(4-chlorobenzoyl)-N'-(1-methyl-2-phenyl)ethylthiourea.

7. A thiourea as claimed in claim 1 which is N-furoyl-N'-(1-methyl-2-phenyl)ethylthiourea.

8. A thiourea as claimed in claim 1 which is N-(3-toluoyl)-N'-(1-methyl-2-phenyl)ethylthiourea.

* * * * *